(12) United States Patent
Clark

(10) Patent No.: US 8,002,886 B2
(45) Date of Patent: Aug. 23, 2011

(54) FLUOROCHEMICAL URETHANE COMPOUNDS HAVING PENDENT SILYL GROUPS USED FOR SURFACE TREATMENT

(75) Inventor: Gregory D. Clark, Silver Spring, MD (US)

(73) Assignee: 3M Innovative Properties Company, St. Paul, MN (US)

( * ) Notice: Subject to any disclaimer, the term of this patent is extended or adjusted under 35 U.S.C. 154(b) by 116 days.

(21) Appl. No.: 12/444,863

(22) PCT Filed: Nov. 21, 2007

(86) PCT No.: PCT/US2007/085340
§ 371 (c)(1),
(2), (4) Date: Apr. 9, 2009

(87) PCT Pub. No.: WO2008/073689
PCT Pub. Date: Jun. 19, 2008

(65) Prior Publication Data
US 2010/0089290 A1      Apr. 15, 2010

Related U.S. Application Data

(60) Provisional application No. 60/870,300, filed on Dec. 15, 2006.

(51) Int. Cl.
*D06M 15/643* (2006.01)
(52) U.S. Cl. .................. 106/287.11; 556/414
(58) Field of Classification Search ............. 106/287.11; 556/414
See application file for complete search history.

(56) References Cited

U.S. PATENT DOCUMENTS

| | | | |
|---|---|---|---|
| 3,493,424 A | 2/1970 | Mohrlok et at | |
| 3,950,588 A | 4/1976 | McDougal | |
| 4,351,736 A | 9/1982 | Steinberger et al. | |
| 4,508,916 A | 4/1985 | Newell et al. | |
| 4,781,844 A | 11/1988 | Kortmann et al. | |
| 5,073,442 A | 12/1991 | Knowlton et al. | |
| 5,274,159 A | 12/1993 | Pellerite et al. | |
| 6,664,354 B2 | 12/2003 | Savu et al. | |
| 7,294,731 B1 | 11/2007 | Flynn et al. | |
| 7,652,116 B2 * | 1/2010 | Clark et al. | 528/28 |
| 7,652,117 B2 * | 1/2010 | Clark et al. | 528/28 |
| 2002/0192380 A1 | 12/2002 | Elsbernd et al. | |
| 2004/0077775 A1 | 4/2004 | Audenaert et al. | |
| 2004/0176600 A1 | 9/2004 | Juhue et al. | |

FOREIGN PATENT DOCUMENTS

| | | |
|---|---|---|
| EP | 0 529 895 A1 | 3/1993 |
| EP | 0 933 377 A2 | 8/1999 |
| WO | 2005/121156 A1 | 12/2005 |

OTHER PUBLICATIONS

K.K. Dietliker in Chemistry & Technology of UV & EB Formulation for Coatings, Inks & Paints, vol. 3, pp. 276-298, Sita Technology Ltd., London (1991).

* cited by examiner

*Primary Examiner* — Andrew D Kosar
*Assistant Examiner* — Valerie Rodriguez-Garcia
(74) *Attorney, Agent, or Firm* — Kent S. Kokko

(57) ABSTRACT

Fluorochemical urethane compounds and coating compositions derived therefrom are described. The compounds and composition may be used in treating substrates, in particular substrates having a hard surface such as ceramics or glass, to render them water, oil, stain, and/or dirt repellent. The compounds have the formula $(R_f)_x R_1 —(R^2)_y]_z$ wherein $R_f$ is a fluorine-containing group, $R^1$ is the residue of a polyisocyanate. $R^2$ is of the formula $—NH—CO—X^1—R^3(CH_2CH_2—S—R^5—Si(Y)_p(R^6)_{3p})_q$ wherein $X^1$ is $—O—$ or $—NR^4—$, where $R^4$ is H or $C_1$-$C_4$ alkyl, $R^3$ is a polyvalent alkylene or arylene group, or combinations thereof, said alkylene groups optionally containing one or more catenary oxygen atoms, $R^5$ is a divalent alkylene group, said alkylene group optionally containing one or more catenary oxygen atoms, Y is a hydrolysable group, $R^6$ is a monovalent alkyl or aryl group, p is 1, 2 or 3, q is 1 to 5, x and y are each independently at least 1, and z is 1 or 2.

14 Claims, No Drawings

FLUOROCHEMICAL URETHANE COMPOUNDS HAVING PENDENT SILYL GROUPS USED FOR SURFACE TREATMENT

CROSS REFERENCE TO RELATED APPLICATIONS

This application is a national stage filing under 35 U.S.C. 371 of PCT/US2007/085340, filed Nov. 21, 2007, which claims priority to Provisional Application No. 60/870,300, filed Dec. 15, 2006, the disclosure of which is incorporated by reference in its/their entirety herein.

FIELD OF THE INVENTION

The present invention relates to fluorochemical urethane compounds and coating compositions derived therefrom, which may be used in treating substrates, in particular substrates having a hard surface such as ceramics or glass, to render them water, oil, stain, and dirt repellent.

BACKGROUND

Although many fluorinated compositions are known in the art for treating substrates to render them oil and water repellent, there continues to be a desire to provide further improved compositions for the treatment of substrates, in particular substrates having a hard surface such as ceramics, glass and stone, in order to render them water-repellent, oil-repellent, and easy to clean. There is also a need for treating glass and plastic as a hard surfaces, particularly in the optical field, in order to render them stain, dirt and dust resistant. Desirably, such compositions and methods employing them can yield coatings that have improved properties. In particular, it would be desirable to improve the durability of the coating, including an improved abrasion resistance of the coating. Furthermore, improving the ease of cleaning of such substrates while using less detergents, water or manual labor, is not only a desire by the end consumer, but has also a positive impact on the environment. Also, it is desired that the coatings show particularly good chemical and solvent resistance. The compositions may be applied in an easy and safe way and are compatible with existing manufacturing methods. Preferably, the compositions will fit easily into the manufacturing processes that are practiced to produce the substrates to be treated.

SUMMARY

The present invention provides fluorochemical urethane compounds of the formula

(I)

wherein $R_f$ is a fluorine-containing group, including perfluoroalkyl, perfluorooxyalkyl, perfluoroalkylene and perfluorooxyalkylene groups,
$R^1$ is the residue of a polyisocyanate having a valence of x+y;
$R^2$ is a silane-containing moiety derived from the free-radical addition reaction between a thiosilane and an ethylenically unsaturated group pendant from the polyisocyanate residue, such as vinyl, allyl or allyloxy groups;
x and y are each independently at least 1, and z is 1 or 2

In one aspect, this invention relates to chemical compositions comprising one or more compounds (where z is 1) or oligomers (where z is 2) and mixtures thereof having at least one fluorine-containing group and at least one silane-containing moiety derived from the addition reaction between a thiosilane and an ethylenically unsaturated group pendant from the polyisocyanate residue.

As used herein, the term "oligomer" means a polymer molecule consisting of only a few, i.e. up to an average of 10 repeating (polymerized) or repeatable units. Each repeating unit comprises a residue of a polyisocyanate that is derived from the reaction of at least one difunctional, nucleophilic, fluorine-containing compound, thiosilane and polyisocyanate, wherein the fluorine-containing moiety is selected from the group consisting of perfluoroalkyl, perfluoroalkylene, perfluorooxyalkyl, and perfluorooxyalkylene. The oligomer may be terminated with one or more perfluoroalkyl groups, one or more perfluorooxyalkyl groups, and/or one of more silyl groups.

These compounds or oligomers may comprise the free-radical addition reaction product of an thiosilane with a fluorine-containing urethane compound having pendent ethylenically unsaturated group groups, said urethane compound comprising the reaction product of a polyisocyanate, a nucleophilic fluorinated compound having one or two nucleophilic, isocyanate-reactive functional groups, and at least one nucleophilic ethylenically unsaturated compound. In another embodiment, the compounds may comprise the addition reaction product of a thiosilane with a nucleophilic, ethylenically unsaturated compound, and subsequent reaction product with the polyisocyanate and the fluorine-containing compound.

Unless otherwise stated, the following terms used in the specification and claims have the meanings given below:

"Alkyl" means a linear or branched, cyclic or acylic, saturated monovalent hydrocarbon radical having from one to about twelve carbon atoms, e.g., methyl, ethyl, 1-propyl, 2-propyl, pentyl, and the like.

"Alkylene" means a linear saturated divalent hydrocarbon radical having from one to about twelve carbon atoms or a branched saturated divalent hydrocarbon radical having from three to about twelve carbon atoms, e.g., methylene, ethylene, propylene, 2-methylpropylene, pentylene, hexylene, and the like.

"Alkoxy" means an alkyl having a terminal oxygen atom, e.g. $CH_3$—O—, $C_2H_5$—O—, and the like.

"Aralkylene" means an alkylene radical defined above with an aromatic group attached to the alkylene radical, e.g., benzyl, pyridylmethyl, 1-naphthylethyl, and the like. "Cured chemical composition" means that the chemical composition is dried or solvent has evaporated from the chemical composition from ambient temperature or higher until dryness, up to approximately 24 hours. The composition may further be crosslinked as result of siloxane bonds formed between the urethane compounds.

"Fluorocarbon nucleophilic compound" means a compound having one or two nucleophilic, isocyanate-reactive functional groups, such as a hydroxyl group or an amine group, and a perfluoroalkyl, perfluoroalkylene, perfluorooxyalkyl or perfluorooxyalkylene group, e.g. $CF_9SO_2N(CH_3)CH_2CH_2OH$, $C_4F_9CH_2CH_2OH$, $C_2F_5O(C_2F_4O)_3CF_2CONHC_2H_4OH$, c-$C_6F_{11}CH_2OH$, $HOCH_2CH_2C_4F_8CH_2CH_2OH$, and the like.

"Fluorochemical urethane compounds" refers to compounds of Formula I, and will include those having urethane linkages per se, or alternatively urea and/or thiourea linkages.

"Hard substrate" means any rigid material that maintains its shape, e.g., glass, ceramic, concrete, natural stone, wood, metals, plastics, and the like.

"Oxyalkoxy" has essentially the meaning given above for alkoxy except that one or more oxygen atoms may be present in the alkyl chain and the total number of carbon atoms present may be up to 50, e.g. $CH_3CH_2OCH_2CH_2O-$, $C_4H_9OCH_2CH_2OCH_2CH_2O-$, $CH_3O(CH_2CH_2O)_nH$, and the like.

"Oxyalkyl" has essentially the meaning given above for alkyl except that one or more oxygen heteroatoms may be present in the alkyl chain, these heteroatoms being separated from each other by at least one carbon, e.g., $CH_3CH_2OCH_2CH_2-$, $CH_3CH_2OCH_2CH_2OCH(CH_3)CH_2-$, $C_4F_9CH_2OCH_2CH_2-$, and the like.

"Oxyalkylene" has essentially the meaning given above for alkylene except that one or more oxygen heteroatoms may be present in the alkylene chain, these heteroatoms being separated from each other by at least one carbon, e.g., $-CH_2OCH_2O-$, $-CH_2CH_2OCH_2CH_2-$, $-CH_2CH_2OCH_2CH_2CH_2-$, and the like.

"Halo" means fluoro, chloro, bromo, or iodo, preferably fluoro and chloro.

"Perfluoroalkyl" has essentially the meaning given above for "alkyl" except that all or essentially all of the hydrogen atoms of the alkyl radical are replaced by fluorine atoms and the number of carbon atoms is from 1 to about 12, e.g. perfluoropropyl, perfluorobutyl, perfluorooctyl, and the like.

"Perfluoroalkylene" has essentially the meaning given above for "alkylene" except that all or essentially all of the hydrogen atoms of the alkylene radical are replaced by fluorine atoms, e.g., perfluoropropylene, perfluorobutylene, perfluorooctylene, and the like.

"Perfluorooxyalkyl" has essentially the meaning given above for "oxyalkyl" except that all or essentially all of the hydrogen atoms of the oxyalkyl radical are replaced by fluorine atoms and the number of carbon atoms is from 3 to about 100, e.g. $CF_3CF_2OCF_2CF_2-$, $CF_3CF_2O(CF_2CF_2O)_3CF_2CF_2-$, $C_3F_7O(CF(CF_3)CF_2O)_sCF(CF_3)CF_2-$, where s is (for example) from about 1 to about 50, and the like.

"Perfluorooxyalkylene" has essentially the meaning given above for "oxyalkylene" except that all or essentially all of the hydrogen atoms of the oxyalkylene radical are replaced by fluorine atoms, and the number of carbon atoms is from 3 to about 100, e.g., $-CF_2OCF_2-$, or $-[CF_2-CF_2-O]_r-[CF(CF_3)-CF_2-O]_s-$; wherein r and s are (for example) integers of 1 to 50.

"Perfluorinated group" means an organic group wherein all or essentially all of the carbon bonded hydrogen atoms are replaced with fluorine atoms, e.g. perfluoroalkyl, perfluorooxyalkyl, and the like.

"Polyfunctional isocyanate compound" or "polyisocyanate" means a compound containing an average of greater than one, preferably two or more isocyanate groups, —NCO, attached to a multivalent organic group, e.g. hexamethylene diisocyanate, the biuret and isocyanurate of hexamethylene diisocyanate, and the like.

"Nucleophilic ethylenically unsaturated compound" means an organic compound with at least one primary or secondary hydroxyl group per molecule, and at least one ethylenically unsaturated group, including vinyl, allyl and allyloxy groups.

DETAILED DESCRIPTION

The present invention provides novel fluorochemical urethane compound of the formula:

wherein
$R_f$ is a fluorine-containing group, comprising a monovalent perfluoroalkyl or a perfluorooxyalkyl group, or a divalent perfluoroalkylene or a perfluorooxyalkylene group,
$R^1$ is the residue of a polyisocyanate,
$R^2$ is of the formula:

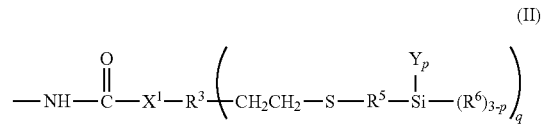

wherein
$X^1$ is —O— or —NR$^4$—, where $R^4$ is H or $C_1$-$C_4$ alkyl,
$R^3$ is a polyvalent alkylene or arylene groups, or combinations thereof, said alkylene groups optionally containing one or more catenary oxygen atoms;
$R^5$ is a divalent alkylene group, said alkylene groups optionally containing one or more catenary oxygen atoms;
Y is a hydrolysable group,
$R^6$ is a monovalent alkyl or aryl group,
p is 1, 2 or 3, preferably 3, and
q is 1 to 5, preferably 2 to 5,
x and y are each independently at least 1, and z is 1 or 2.

Although the inventors do not wish to be bound by theory, compounds of the above formula I are believed to undergo a condensation reaction with the substrate surface to form a siloxane layer via hydrolysis or displacement of the hydrolysable "Y" groups of Formula II. In this context, "siloxane" refers to —Si—O—Si— bonds to which are attached to compounds of Formula I. In the presence of water, the "Y" groups will undergo hydrolysis "Si—OH" groups, and further condensation to siloxanes.

A coating prepared from the coating composition that includes compounds of Formula I includes the perfluoropolyether silanes per se, as well as siloxane derivatives resulting from bonding to the surface of a preselected substrate. The coatings can also include unreacted or uncondensed "Si—Y" groups. The composition may further contain may also contain non-silane materials such as oligomeric perfluoropolyether monohydrides, starting materials and perfluoropolyether alcohols and esters. Likewise, coated fluorochemical urethanes may include the silanes of Formula I per se, as well as the siloxane derivatives resulting from reaction with the substrate surface.

In one embodiment, the invention provides a coating composition comprising the compound of Formula I, a solvent, and optionally water and an acid. In another embodiment, the coating composition comprises an aqueous suspension or dispersion of the compounds. To achieve good durability for many substrates, such as ceramics, the compositions of the present invention preferably include water. Thus the present invention provides a method of coating comprising the steps of providing contacting a substrate with a coating composition comprising the compound of Formula I and a solvent. The coating composition may further comprise water and an acid. In one embodiment the method comprises contacting a substrate with a coating composition comprising the silane of Formula I and a solvent, and subsequently contacting the substrate with an aqueous acid.

Polyisocyanate compounds useful in preparing the fluorochemical compounds comprise isocyanate groups attached to the multivalent organic group that can comprise a multivalent aliphatic, alicyclic, or aromatic moiety ($R^1$); or a multivalent aliphatic, alicyclic or aromatic moiety attached to a biuret, an isocyanurate, or a uretdione, or mixtures thereof. Preferred polyfunctional isocyanate compounds contain at least two isocyanate (—NCO) radicals. Compounds containing at least two —NCO radicals are preferably comprised of di- or trivalent aliphatic, alicyclic, araliphatic, or aromatic groups to which the —NCO radicals are attached. Aliphatic di- or trivalent groups are preferred.

Representative examples of suitable polyisocyanate compounds include isocyanate functional derivatives of the polyisocyanate compounds as defined herein. Examples of derivatives include, but are not limited to, those selected from the group consisting of ureas, biurets, allophanates, dimers and trimers (such as uretdiones and isocyanurates) of isocyanate compounds, and mixtures thereof. Any suitable organic polyisocyanate, such as an aliphatic, alicyclic, araliphatic, or aromatic polyisocyanate, may be used either singly or in mixtures of two or more.

The aliphatic polyisocyanate compounds generally provide better light stability than the aromatic compounds. Aromatic polyisocyanate compounds, on the other hand, are generally more economical and reactive toward nucleophiles than are aliphatic polyisocyanate compounds. Suitable aromatic polyisocyanate compounds include, but are not limited to, those selected from the group consisting of 2,4-toluene diisocyanate (TDI), 2,6-toluene diisocyanate, an adduct of TDI with trimethylolpropane (available as Desmodur™ CB from Bayer Corporation, Pittsburgh, Pa.), the isocyanurate trimer of TDI (available as Desmodur™ IL from Bayer Corporation, Pittsburgh, Pa.), diphenylmethane 4,4'-diisocyanate (MDI), diphenylmethane 2,4'-diisocyanate, 1,5-diisocyanato-naphthalene, 1,4-phenylene diisocyanate, 1,3-phenylene diisocyanate, 1-methyoxy-2,4-phenylene diisocyanate, 1-chlorophenyl-2,4-diisocyanate, and mixtures thereof.

Examples of useful alicyclic polyisocyanate compounds include, but are not limited to, those selected from the group consisting of dicyclohexylmethane diisocyanate ($H_{12}$ MDI, commercially available as Desmodur™ available from Bayer Corporation, Pittsburgh, Pa.), 4,4'-isopropyl-bis(cyclohexylisocyanate), isophorone diisocyanate (IPDI), cyclobutane-1,3-diisocyanate, cyclohexane 1,3-diisocyanate, cyclohexane 1,4-diisocyanate (CHDI), 1,4-cyclohexanebis(methylene isocyanate) (BDI), dimmer acid diisocyanate (available from Bayer),1,3-bis(isocyanatomethyl)cyclohexane ($H_6$ XDI), 3-isocyanatomethyl-3,5,5-trimethylcyclohexyl isocyanate, and mixtures thereof.

Examples of useful aliphatic polyisocyanate compounds include, but are not limited to, those selected from the group consisting of tetramethylene 1,4-diisocyanate, hexamethylene 1,4-diisocyanate, hexamethylene 1,6-diisocyanate (HDI), octamethylene 1,8-diisocyanate, 1,12-diisocyanatododecane, 2,2,4-trimethyl-hexamethylene diisocyanate (TMDI), 2-methyl-1,5-pentamethylene diisocyanate, dimer diisocyanate, the urea of hexamethylene diisocyanate, the biuret of hexamethylene 1,6-diisocyanate (HDI) (Desmodur™ N-100 and N-3200 from Bayer Corporation, Pittsburgh, Pa.), the isocyanurate of HDI (available as Desmodur™ N-3300 and Desmodur™N-3600 from Bayer Corporation, Pittsburgh, Pa.), a blend of the isocyanurate of HDI and the uretdione of HDI (available as Desmodure™ N-3400 available from Bayer Corporation, Pittsburgh, Pa.), and mixtures thereof.

Examples of useful araliphatic polyisocyanates include, but are not limited to, those selected from the group consisting of m-tetramethyl xylylene diisocyanate (m-TMXDI), p-tetramethyl xylylene diisocyanate (p-TMXDI), 1,4-xylylene diisocyanate (XDI), 1,3-xylylene diisocyanate, p-(1-isocyanatoethyl)phenyl isocyanate, m-(3-isocyanatobutyl)phenyl isocyanate, 4-(2-isocyanatocyclohexyl-methyl)phenyl isocyanate, and mixtures thereof.

Preferred polyisocyanates, in general, include those selected from the group consisting of tetramethylene 1,4-diisocyanate, hexamethylene 1,4-diisocyanate, hexamethylene 1,6-diisocyanate (HDI), octamethylene 1,8-diisocyanate, 1,12-diisocyanatododecane, and the like, and mixtures thereof. Fluorochemical compositions of the present invention comprising compounds or oligomers made with preferred polyisocyanates impart both high water and hexadecane receding dynamic contact angles. High water receding dynamic contact angle together with high hexadecane receding dynamic contact angle is typically predictive of good water-repellency and oil-repellency properties.

The fluorochemical urethane comprises, in part, the reaction product of a fluorinated compound having a mono- or difunctional perfluorinated group, and at least one nucleophilic, isocyanate-reactive functional group (herein a "nucleophilic fluorinated compound"). Such compounds include those of the formula:

where
$R_f^1$ is a monovalent perfluoroalkyl or a perfluorooxyalkyl group, or a divalent perfluoroalkylene or a perfluorooxyalkylene group,
Q is a covalent bond, or a polyvalent alkylene group of valency z, said alkylene optionally containing one or more catenary (in-chain) nitrogen or oxygen atoms, and optionally containing one or more sulfonamide, carboxamido, or carboxy functional groups,
$X^2$ is —O—, —$NR^4$— or —S—, where $R^4$ is H or $C_1$-$C_4$ alkyl,
y is 1 or 2, and
z is 1 or 2.

With respect to Formulas I and III, the reaction between the nucleophilic fluorinated compound (III) and an isocyanate group of a polyisocyanate produces a group of the formula

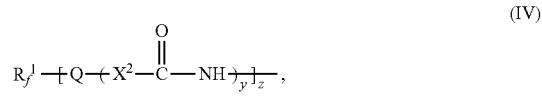

where $R_f^1$, Q, $X^2$, y and z are as previously defined for Formula III.

The $R_f^1$ groups of Formula III and IV can contain straight chain, branched chain, or cyclic fluorinated groups or any combination thereof, and can be mono- or divalent. The $R_f^1$ groups can optionally contain one or more catenary oxygen atoms in the carbon-carbon chain so as to form a carbon-oxygen-carbon chain (i.e. a oxyalkylene group). Fully-fluorinated groups are generally preferred, but hydrogen or chlorine atoms can also be present as substituents, provided that no more than one atom of either is present for every two carbon atoms.

It is additionally preferred that any $R_f^1$ group contain at least about 40% fluorine by weight, more preferably at least about 50% fluorine by weight. The terminal portion of the monovalent $R_f^1$ group is generally fully-fluorinated, preferably containing at least three fluorine atoms, e.g., $CF_3—$, $CF_3CF_2—$, $CF_3CF_2CF_2—$, $(CF_3)_2N—$, $(CF_3)_2CF—$, $SF_5CF_2—$. In certain embodiments, monovalent perfluoroalkyl groups (i.e., those of the formula $C_nF_{2n+1}—$) or divalent perfluoroalkylene groups (i.e., those of the formula $—C_nF_{2n}—$) wherein n is 2 to 12 inclusive are the preferred $R_f^1$ groups, with n=3 to 5 being more preferred and with n=4 being the most preferred.

Useful perfluorooxyalkyl and perfluorooxyalkylene groups correspond to the formula:

$$W—R_f^3—O—R_f^4—(R_f^5)_q—\qquad(V)$$

wherein
W is F (fluorine) for monovalent perfluorooxyalkyl, and an open valence ("–") for divalent perfluorooxyalkylene;
$R_f^3$ represents a perfluoroalkylene group, $R_f^4$ represents a perfluoroalkyleneoxy group consisting of perfluoroalkyleneoxy groups having 1, 2, 3 or 4 carbon atoms or a mixture of such perfluoroalkyleneoxy groups, $R_f^5$ represents a perfluoroalkylene group and q is 0 or 1. The perfluoroalkylene groups $R_f^3$ and $R_f^5$ in formula (IV) may be linear or branched and may comprise 1 to 10 carbon atoms, preferably 1 to 6 carbon atoms. A typical monovalent perfluoroalkyl group is $CF_3—CF_2—CF_2—$ and a typical divalent perfluoroalkylene is $—CF_2—CF_2—CF_2—$, $—CF_2—$ or $—CF(CF_3)—$. Examples of perfluoroalkyleneoxy groups $R_f^4$ include: $—CF_2—CF_2—O—$, $—CF(CF_3)—CF_2—O—$, $—CF_2—CF(CF_3)—O—$, $—CF_2—CF_2—CF_2—O—$, $—CF_2—O—$, $—CF(CF_3)—O—$, and $—CF_2—CF_2—CF_2—O$, which may repeat, for example, from 3 to 30 times.

The perfluoroalkyleneoxy group $R_f^4$ may be comprised of the same perfluorooxyalkylene units or of a mixture of different perfluorooxyalkylene units. When the perfluorooxyalkylene group is composed of different perfluoroalkylene oxy units, they can be present in a random configuration, alternating configuration or they can be present as blocks. Typical examples of perfluorinated poly(oxyalkylene) groups include: $—[CF_2—CF_2—O]_r—$; $—[CF(CF_3)—CF_2—O]_s—$; $—[CF_2CF_2—O]_r—[CF_2O]_t—$, $—[CF_2CF_2CF_2CF_2—O]_u$ and $—[CF_2—CF_2—O]_r—[CF(CF_3)—CF_2—O]_s—$; wherein each of r, s, t and u each are integers of 1 to 50, preferably 2 to 25. A preferred perfluorooxyalkyl group that corresponds to formula (V) is $CF_3—CF_2—CF_2—O—[CF(CF_3)—CF_2O]_s—CF(CF_3)CF_2—$ wherein s is an integer of 1 to 50.

Perfluorooxyalkylene and perfluorooxyalkyl compounds can be obtained by oligomerization of hexafluoropropylene oxide that results in a terminal carbonyl fluoride group. This carbonyl fluoride may be converted into an acid, ester or alcohol by reactions well known to those skilled in the art. The carbonyl fluoride or acid, ester or alcohol derived therefrom may then be reacted further to introduce the desired isocyanate reactive groups according to known procedures.

With respect to Formula I to III, where x or z is 1, nucleophilic fluorochemical monofunctional compounds, such as monoalcohols and monoamines are contemplated. Representative examples of useful fluorochemical monofunctional compounds include the following:
$CF_3(CF_2)_3SO_2N(CH_3)CH_2CH_2OH$, $CF_3(CF_2)_3SO_2N(CH_3)CH(CH_3)CH_2OH$, $CF_3(CF_2)_3SO_2N(CH_3)CH_2CH(CH_3)NH_2$, $CF_3(CF_2)_3SO_2N(CH_2CH_3)CH_2CH_2SH$, $CF_3(CF_2)_3SO_2N(CH_3)CH_2CH_2SCH_2CH_2OH$, $C_6F_{13}SO_2N(CH_3)(CH_2)_4OH$, $CF_3(CF_2)_7SO_2N(H)(CH_2)_3OH$, $C_3F_7SO_2N(CH_3)CH_2CH_2OH$, $CF_3(CF_2)_4SO_2N(CH_3)(CH_2)_4NH_2$, $C_4F_9SO_2N(CH_3)(CH_2)_{11}OH$, $CF_3(CF_2)_5SO_2N(CH_2CH_3)CH_2CH_2OH$, $CF_3(CF_2)_5SO_2N(C_2H_5)(CH_2)_6OH$, $CF_3(CF_2)_2SO_2N(C_2H_5)(CH_2)_4OH$, $CF_3(CF_2)_3SO_2N(C_3H_7)CH_2OCH_2CH_2CH_2OH$, $CF_3(CF_2)_4SO_2N(CH_2CH_2CH_3)CH_2CH_2OH$, $CF_3(CF_2)_4SO_2N(CH_2CH_2CH_3)CH_2CH_2NHCH_3$, $CF_3(CF_2)_3SO_2N(C_4H_9)CH_2CH_2NH_2$, $CF_3(CF_2)_3SO_2N(C_4H_9)(CH_2)4SH$, $CF_3(CF_2)_3CH_2CH_2OH$, $C_4F_9OC_2F_4OCF_2CH_2OCH_2CH_2OH$; $n-C_6F_{13}CF(CF_3)CON(H)CH_2CH_2OH$; $C_6F_{13}CF(CF_3)CO_2C_2H_4CH(CH_3)OH$; $C_3F_7CON(H)CH_2CH_2OH$; $C_3F_7O(CF(CF_3)CF_2O)_{1-36}CF(CF_3)CH_2OH$; and the like, and mixtures thereof. If desired, other isocyanate-reactive functional groups may be used in place of those depicted.

With respect to Formulas I to III, where x or z is 2, fluorinated polyols are preferred. Representative examples of suitable fluorinated polyols include $R_f^1SO_2N(CH_2CH_2OH)_2$ such as N-bis(2-hydroxyethyl)perfluorobutylsulfonamide; $R_f^1OC_6H_4SO_2N(CH_2CH_2OH)_2$; $R_f^1SO_2N(R')CH_2CH(OH)CH_2OH$ such as $C_6F_{13}SO_2N(C_3H_7)CH_2CH(OH)CH_2OH$; $R_f^1CH_2CON(CH_2CH_2OH)_2$; $R_f^1CON(CH_2CH_2OH)_2$; $CF_3CF_2(OCF_2CF_2)_3OCF_2CON(CH3)CH2CH(OH)CH2OH$; $R_f^1OCH_2CH(OH)CH_2OH$ such as $C_4F_9OCH_2CH(OH)CH_2OH$; $R_f^1CH_2CH_2SC_3H_6OCH_2CH(OH)CH_2OH$; $R_f^1CH_2CH_2SC_3H_6CH(CH_2OH)_2$; $R_f^1CH_2CH_2SCH_2CH(OH)CH_2OH$; $R_f^1CH_2CH_2SCH(CH_2OH)CH_2CH_2OH$; $R_f^1CH_2CH_2CH_2SCH_2CH(OH)CH_2OH$ such as $C_5F_{11}(CH_2)_3SCH_2CH(OH)CH_2OH$; $R_f^1CH_2CH_2CH_2OCH_2CH(OH)CH_2OH$ such as $C_5F_{11}(CH_2)_3OCH_2CH(OH)CH_2OH$; $R_f^1CH_2CH_2CH_2OC_2H_4OCH_2CH(OH)CH_2OH$; $R_f^1CH_2CH_2(CH_3)OCH_2CH(OH)CH_2OH$; $R_f^1(CH_2)_4SC_3H_6CH(CH_2OH)CH_2OH$; $R_f^1(CH_2)_4SCH_2CH(CH_2OH)_2$; $R_f^1(CH_2)_4SC_3H_6OCH_2CH(OH)CH_2OH$; $R_f^1CH_2CH(C_4H_9)SCH_2CH(OH)CH_2OH$; $R_f^1CH_2OCH_2CH(OH)CH_2OH$; $R_f^1CH2CH(OH)CH_2SCH_2CH_2OH$; $R_f^1CH_2CH(OH)CH_2SCH_2CH_2OH$; $R_f^1CH_2CH(OH)CH_2OCH_2CH_2OH$; $R_f^1CH_2CH(OH)CH_2OH$; $R_f^1R''SCH(R'''OH)CH(R'''OH)SR''R_f$; $(R_f^1CH_2CH_2SCH_2CH_2SCH_2)_2C(CH_2OH)_2$; $((CF_3)_2CFO(CF_2)_2(CH_2)_2SCH_2)_2C(CH_2OH)_2$; $(R_f^1R''SCH_2)_2C(CH_2OH)_2$; 1,4-bis(1-hydroxy-1,1-dihydroperfluoroethoxyethoxy)perfluoro-n-butane $(HOCH_2CF_2OC_2F_4O(CF_2)_4OC_2F_4OCF_2CH_2OH)$; 1,4-bis(1-hydroxy-1,1-dihydroperfluoropropoxy)perfluoro-n-butane $(HOCH_2CF_2CF_2O(CF_2)_4OCF_2CF_2CH_2OH)$; fluorinated oxetane polyols made by the ring-opening polymerization of fluorinated oxetane such as Poly-3-Fox™ (available from Omnova Solutions, Inc., Akron Ohio); polyetheralcohols prepared by ring opening addition polymerization of a fluorinated organic group substituted epoxide with a compound containing at least two hydroxyl groups as described in U.S. Pat. No. 4,508,916 (Newell et al); and perfluoropolyether diols such as Fomblin™ ZDOL $(HOCH_2CF_2O(CF_2O)_{8-12}(CF_2CF_2O)_{8-12}CF_2CH_2OH$, available from Ausimont); wherein $R_f^1$ is a perfluoroalkyl group having 1 to 12 carbon atoms, or a perfluorooxyalkyl group having 3 to about 50 carbon atoms with all perfluorocarbon chains present having 6 or fewer carbon atoms, or mixtures thereof; R' is alkyl of 1 to 4 carbon atoms; R'' is branched or straight chain alkylene of 1 to 12 carbon atoms, alkylenethioalkylene of 2 to 12 carbon atoms, alkylene-oxyalkylene of 2 to 12 carbon atoms, or alkylene iminoalkylene of 2 to 12 carbon atoms, where the nitrogen atom contains as a third substituent hydrogen or alkyl of 1 to 6 carbon atoms; and R''' is a straight or branched chain alkylene of 1 to 12 carbon atoms or an alkylene-polyoxyalkylene of formula $C_rH_{2r}(OC_sH_{2s})_t$ where r is 1-12, s is 2-6, and t is 1-40.

Preferred fluorinated polyols include N-bis(2-hydroxyethyl) perfluorobutylsulfonamide; fluorinated oxetane polyols made by the ring-opening polymerization of fluorinated oxetane such as Poly-3-Fox™ (available from Omnova Solutions, Inc., Akron Ohio); polyetheralcohols prepared by ring opening addition polymerization of a fluorinated organic group substituted epoxide with a compound containing at least two hydroxyl groups as described in U.S. Pat. No. 4,508,916 (Newell et al); perfluoropolyether diols such as Fomblin™ ZDOL $(HOCH_2CF_2O(CF_2O)_{8-12}(CF_2CF_2O)_{8-12}CF_2CH_2OH$, available from Ausimont); 1,4-bis(1-hydroxy-1,1-dihydroperfluoroethoxyethoxy)perfluoro-n-butane $(HOCH_2CF_2OC_2F_4O(CF_2)_4OC_2F_4OCF_2CH_2OH)$; and 1,4-bis(1-hydroxy-1,1-dihydroperfluoropropoxy)perfluoro-n-butane $(HOCH_2CF_2CF_2O(CF_2)_4OCF_2CF_2CH_2OH)$.

More preferred polyols comprised of at least one fluorine-containing group include N-bis(2-hydroxyethyl)perfluorobutylsulfonamide; 1,4-bis(1-hydroxy-1,1-dihydroperfluoropropoxy)perfluoro-n-butane $(HOCH_2CF_2CF_2O(CF_2)_4OCF_2CF_2CH_2OH)$ and $CF_3CF_2CF_2$—O—$[CF(CF_3)CF_2O]_{3-25}$—$CF(CF_3)$—. This perfluorinated polyether group can be derived from an oligomerization of hexafluoropropylene oxide. Such perfluorinated polyether groups are preferred in particular because of their benign environmental properties.

The fluorochemical urethane comprises, in part, the reaction product of a nucleophilic ethylenically unsaturated compound having an isocyanate-reactive, nucleophilic functional group and least one ethylenically unsaturated group (hereinafter a "nucleophilic unsaturated compound"). The unsaturated group may be a vinyl, allyl or allyloxy and the nucleophilic functional group may be an amino or hydroxy group. Preferably the unsaturated group is not a vinyloxy group, e.g. $CH_2$=$CHO$—. Preferably, the nucleophilic unsaturated compound is a polyunsaturated compound having a hydroxyl group and at least two unsaturated groups.

Such compounds include those of the formula:

wherein
$X^1$ is —O— or —$NR^4$—, where $R^4$ is H or $C_1$-$C_4$ alkyl,
$R^3$ is a divalent alkylene or arylene groups, or combinations thereof, said alkylene groups optionally containing one or more catenary oxygen atoms; and
q is 1 to 5.

Preferably q is greater than 1. The resulting nucleophilic polyunsaturated compounds allow the addition of multiple silane groups to the urethane compound. The molar ratio of silane groups to —NH—C(O)—$X^1$— groups may be greater than 1:1, or greater than 2:1. Preferably $HX^1$— is not directly connected to an aromatic ring, such as with a phenolic compound.

Compounds of Formula VI include terminally mono-, di- or poly-unsaturated ethers of polyols such as 1,3-butylene glycol, 1,4-butanediol, 1,6-hexanediol, cyclohexane dimethanol, neopentyl glycol, caprolactone modified neopentylglycol hydroxypivalate, diethylene glycol, dipropylene glycol, bisphenol-A, trimethylolpropane, neopentyl glycol, tetraethylene glycol, tricyclodecanedimethanol, triethylene glycol, tripropylene glycol; glycerol, pentaerythritol, and dipentaerythritol pentaacrylate.

Useful nucleophilic unsaturated compounds include hydroxyalkenes such as allyl alcohol, methallyl alcohol, allyloxyethyl alcohol, 2-allyloxymethylpropanol (from dimethylolethane), and 2,2-di(allyloxymethyl)butanol (from trimethylolpropane), as well as the corresponding amines.

The nucleophilic unsaturated compound (VI) may react with a portion of the isocyanate groups of the polyisocyanate to form a urethane compound having pendent unsaturated groups (VI below), which may subsequently be reacted with a thiosilane to form a compound of Formula I.

The reaction product of the nucleophilic unsaturated compound with the isocyanate is of the general formula:

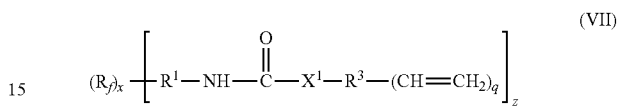

wherein
$R_f$ is a fluorine-containing group, comprising a monovalent perfluoroalkyl or a perfluorooxyalkyl group, or a divalent perfluoroalkylene or a perfluorooxyalkylene group,
$R^1$ is the residue of a polyisocyanate,
$X^1$ is —O— or —$NR^4$—, where $R^4$ is H or $C_1$-$C_4$ alkyl,
$R^3$ is a divalent alkylene or arylene groups, or combinations thereof, said alkylene groups optionally containing one or more catenary oxygen atoms;
x is 1 or 2;
z is 1 or 2, and
q is 1 to 5, preferably 2 to 5.

The fluorochemical urethane compounds comprise, in part, the free radical addition reaction product of a thiosilane with an unsaturated group of the compounds of Formulas VI or VII.

The thiosilane is of the formula

wherein
$R^5$ is a divalent alkylene group, said alkylene groups optionally containing one or more catenary oxygen atoms;
Y is a hydrolysable group,
$R^6$ is a monovalent alkyl or aryl group, and
p is 1, 2 or 3.

Y represents a hydrolysable group in Formula (VIII) such as for example a halide, a $C_1$-$C_4$ alkoxy group, an acyloxy group or a polyoxyalkylene group, such as polyoxyethylene groups as disclosed in U.S. Pat. No. 5,274,159. By hydrolysable it is meant the Y group will undergo an exchange reaction with water to form a Si—OH moiety, which may further react to form siloxane groups. Specific examples of hydrolyzable groups include methoxy, ethoxy and propoxy groups, chlorine and an acetoxy group. $R^6$ is generally non-hydrolyzable.

The thiosilane may be reacted with the nucleophilic unsaturated compound VI or to form an addition product, which may subsequently be reacted with the polyisocyanate (either before or after functionalization by the nucleophilic fluorinated compound. Alternatively, the nucleophilic unsaturated compound of Formula VI may first be reacted with a polyisocyanate to form a urethane compound of Formula VII, followed by free-radical addition of the thiosilane to the ethylenically unsaturated groups pendent from the urethane compound. Preferably, the nucleophilic unsaturated compound is first reacted with the polyisocyanate (again, before or after reaction with the nucleophilic fluorinated compound, to form a urethane compound having pendent unsaturated groups, to which is added the thiosilane by free radical addition. The general reaction schemes are shown below:

$(R_f)_x—R^1—(NCO)_y+(VI)→(VII)$ $(VII)+(VIII)→(I)$ $(VI)+(VIII)→HX^1—R^3—[CH—CH_2—S—R^5—Si(Y)_p(R^6)_{3-p}]_{q(IX)}$ $IX+(R_f)_x—R^1—(NCO)_y→(I)$

Useful thiosilanes include (mercaptomethyl)dimethylethoxysilane, (mercaptomethyl)methyldiethoxysilane, 3-mercaptopropylmethyldimethoxysilane, 3-mercaptopropyltriethoxysilane (mercaptomethyl)methyldiethoxysilane.

The addition of the mercaptosilane (VIII) to either of the ethylenically unsaturated compounds (V or VI) may be effected using free radical initiators. Useful free radical initiators include inorganic and organic peroxides, hydroperoxides, persulfates, azo compounds, redox systems (e.g., a mixture of $K_2S_2O_8$ and $Na_2S_2O_5$), and free radical photoinitiators such as those described by K.K. Dietliker in Chemistry & Technology of UV & EB Formulation for Coatings, Inks & Paints, Volume 3, pages 276-298, SITA Technology Ltd., London (1991). Representative examples include hydrogen peroxide, potassium persulfate, t-butyl hydroperoxide, benzoyl peroxide, t-butyl perbenzoate, cumene hydroperoxide, 2,2'-azobis(2-methylbutyronitrile), (VAZO 67) and azobis (isobutyronitrile) (AIBN). The skilled artisan will recognize that the choice of initiator will depend upon the particular reaction conditions, e.g., choice of solvent.

It will be understood that the free-radical addition of the thiosilane can add to either the least or more substituted carbon atom of the ethylenically unsaturated group, and addition to the less substituted carbon is illustrated in the Figures for convenience. Thus:

$~R^3—CH=CH_2+HS—R^5~→~R^3—CH_2—CH_2—S—R^5~$ and/or $~R^3—CH(CH_3)—S—R^5~$

The fluorochemical compounds can be made by simple blending of the nucleophilic unsaturated compound(s), fluorine-containing nucleophilic compound(s), and the polyisocyanate compound(s), followed by free-radical addition of the thiosilanes to the unsaturated groups. As one skilled in the art would understand, the order of blending or the ordering of the steps is non-limiting and can be modified so as to produce a desired fluorochemical urethane compounds. In one embodiment, for example, the polyisocyanate compound(s), the nucleophilic fluorochemical compound are first reacted with some portion of the isocyanate groups, followed by reaction with the nucleophilic unsaturated compound(s) with some portion of the remaining isocyanate groups, followed by free-radical addition of the thiosilane to the pendent unsaturated groups.

In general, the reactive components and a solvent are charged to a dry reaction vessel in immediate succession or as pre-made mixtures. When a homogeneous mixture or solution is obtained a catalyst is optionally added, and the reaction mixture is heated at a temperature, and for a time sufficient for the reaction to occur. Progress of the reaction can be determined by monitoring the disappearance of the isocyanate peak in the IR.

In general, the nucleophilic compound $R_f—Q(X^2H)_z$ (III), is used in an amount sufficient to react with 5 to 50 mole percent of the available isocyanate functional groups. Preferably, compound III is used to react with 10 to 30 mole percent of the isocyanate groups. The remaining isocyanate groups, about 50 to 95 mole percent, preferably 70 to 90 mole percent is functionalized by the nucleophilic unsaturated compound (VI), followed by free radical addition of the thiosilane (VIII), or alternatively by the reaction product of compounds of Formula VII and VIII, resulting in a urethane compound of Formula I having both pendent fluorochemical groups and pendent silane groups.

Preferably, the ratio of the total number of equivalents of nucleophilic groups (of both the fluorine-containing nucleophilic compounds and nucleophilic unsaturated compounds) to the total number of equivalents of isocyanate groups is about 1:1, i.e. that all or essentially all of the isocyanate groups are reacted.

Depending on reaction conditions (e.g., reaction temperature and/or polyisocyanate used), a catalyst level of up to about 0.5 percent by weight of the reaction mixture may be used may be used to effect the isocyanate condensation reaction, but typically about 0.00005 to about 0.5 percent by weight may be used, 0.02 to 0.1 percent by weight being preferred. In general, if the nucleophilic group is an amine group, a catalyst is not necessary.

Suitable catalysts include, but are not limited to, tertiary amine and tin compounds. Examples of useful tin compounds include tin II and tin IV salts such as stannous octoate, dibutyltin dilaurate, dibutyltin diacetate, dibutyltin di-2-ethylhexanoate, and dibutyltinoxide. Examples of useful tertiary amine compounds include triethylamine, tributylamine, triethylenediamine, tripropylamine, bis(dimethylaminoethyl) ether, morpholine compounds such as ethyl morpholine, and 2,2'-dimorpholinodiethyl ether, 1,4-diazabicyclo[2.2.2]octane (DABCO, Aldrich Chemical Co., Milwaukee, Wis.), and 1,8-diazabicyclo[5.4.0.]undec-7-ene (DBU, Aldrich Chemical Co., Milwaukee, Wis.). Tin compounds are preferred. If an acid catalyst is used, it is preferably removed from the product or neutralized after the reaction. It has been found that the presence of the catalyst may deleteriously affect the contact angle performance.

The fluorochemical compositions of the present invention comprising a mixture of urethane molecules can also be made following a step-wise synthesis, in addition to a batch method. In the synthesis, the polyisocyanate and the fluorinated nucleophilic compound(s) are dissolved together under dry conditions, preferably in a solvent, and then the resulting solution is heated at a temperature sufficient to effect the condensation reaction, optionally in the presence of a catalyst. Pendent fluorine-containing groups are thereby bonded to the isocyanate functional urethane oligomers and compounds.

The resulting isocyanate fluorochemical functional urethane oligomers and compounds are then further reacted with one or more of the nucleophilic unsaturated compounds described above, which added to the above reaction mixture, and react(s) with the remaining or a substantial portion of the remaining isocyanate groups, resulting in a urethane compound having both pendent fluorochemical groups and pendent unsaturated groups.

Compositions according to the present invention may be coated on a substrate and at least partially cured to provide a coated article. In some embodiments, the polymerized coating may form a protective coating that provides at least one of mar resistance, graffiti resistance, stain resistance, adhesive release, low refractive index, and water repellency. Coated articles according to the present invention include, for example, eyeglass lenses, mirrors, windows, adhesive release liners, and anti-graffiti films.

Suitable substrates include, for example, glass (e.g., windows and optical elements such as, for example, lenses and mirrors), ceramic (e.g., ceramic tile), cement, stone, painted surfaces (e.g., automobile body panels, boat surfaces), metal (e.g., architectural columns), paper (e.g., adhesive release liners), cardboard (e.g., food containers), thermosets, thermoplastics (e.g., polycarbonate, acrylics, polyolefins, polyurethanes, polyesters, polyamides, polyimides, phenolic resins, cellulose diacetate, cellulose triacetate, polystyrene, and styrene-acrylonitrile copolymers), and combinations thereof. The substrate may be a film, sheet, or it may have some other form. The substrate may comprise a transparent or translucent display element, optionally having a ceramer or silsesquioxane hardcoat thereon.

In some embodiments, a coating composition comprising a mixture of the fluorochemical urethane compounds and a solvent is provided. The coating compositions of the present invention comprise solvent suspensions, dispersions or solutions of the fluorochemical compounds of the present invention. When applied as coatings, the coating compositions impart oil- and water-repellency properties, and/or stain-release and stain-resistance characteristics to any of a wide variety of substrates.

The fluorochemical compounds can be dissolved, suspended, or dispersed in a variety of solvents to form coating compositions suitable for use in coating onto a substrate. Generally, the solvent solutions can contain from about 0.1 to about 50 weight percent, or even up to about 90 percent non-volatile solids (based on the total weight of the components). Preferably, the coating composition contains about 10 to 30 percent total solids. Coating compositions may contain from about 0.1 to about 10 percent fluorochemical urethane compounds, based on the weight of the solids. Preferably the amount of fluorochemical urethane compounds used in the coating is about 0.1 to about 5 weight percent. For a balance of performance (as measured by contact angles), uniformity of coating and haze, the coating composition most preferably comprises from about 0.1 to about 0.5 weight percent of the fluorochemical urethane. Suitable solvents include alcohols, esters, glycol ethers, amides, ketones, hydrocarbons, hydrofluorocarbons, hydrofluoroethers, chlorohydrocarbons, chlorocarbons, and mixtures thereof.

For ease of manufacturing and for reasons of cost, the compositions of the present invention can be prepared shortly before use by diluting a concentrate of one or more of the fluorinated polyether isocyanate derived silanes. The concentrate will generally comprise a concentrated solution of the compounds of Formula I in an organic solvent. The concentrate should be stable for several weeks, preferably at least 1 month, more preferably at least 3 months. It has been found that the fluorinated isocyanate derived silane can be readily dissolved in an organic solvent at high concentrations.

In some embodiments, the coating composition of the present invention may comprise compounds of Formula I, solvent, water, and optionally an acid. When present, the amount of water typically will be between 0.1 and 20% by weight, preferably between 0.5% by weight and 15% by weight, more preferably between 1 and 10% by weight, relative to the weight of the silane of Formula I.

In some preferred embodiments, the coating solution comprises an aqueous dispersion, solution or suspension of the urethane compounds of Formula I. As result of the high concentration of silyl groups, as when "q" of Formula II is two or greater, the compounds are readily suspended in water. These aqous coating compositions may be prepared by "inverting" an organic solvent solution of the compounds into water by added water, optionally containing a surfactant, and removing the organic solvent under reduced pressure, with agitation. Sonication is a preferred means of agitation the suspensions.

In addition to water, the compositions of the invention may also include an organic or inorganic acid. Organic acids include acetic acid, citric acid, formic acid and the like; fluorinated organic acids, such as $CF_3SO_3H$, $C_3F_7CO_2K$ or those which can be represented by the formula $R_f^2[—(L)_a—Z]_b$ wherein $R_f^2$ represents a mono perfluoroalkyl or perfluorooxy or divalent perfluoroalkylene or perfluoroalkyleneoxy group, L represents an organic divalent linking group, Z represents an acid group, such as carboxylic, sulfonic or phosphonic acid group; a is 0 or 1 and b is 1 or 2.

Examples of suitable $R_f^2$ groups include those given above for $R_f$. Examples of organic acids of formula (IV) include $C_3F_7O(CF(CF_3)CF_2)_{10\text{-}30}CF(CF_3)COOH$, commercially available from DuPont or $CF_3(CF_2)_2OCF(CF_3)COOH$. Examples of inorganic acids include sulfuric acid, hydrochloric acid and the like. The acid will generally be included in the composition in an amount between about 0.01 and 10%, more preferably between 0.05 and 5% by weight, relative to the weight of the silane.

The acid may be formulated into the coating composition per se, or subsequent to coating with the perfluoropolyether silane, the coated substrate may be dipped in an acid solution to effect the formation of a siloxane layer.

The coating compositions of this invention contain silsesquioxanes. Useful silsesquioxanes include co-condensates of diorganooxysilanes (or hydrosylates thereof) of the formula $R^{10}{}_2Si(OR^{11})_2$ with organosilanes (or hydrosylates thereof) of the formula $R^{10}SiO_{3/2}$ where each $R^{10}$ is an alkyl group of 1 to 6 carbon atoms or an aryl group and $R^{11}$ represents an alkyl radical with 1 to 4 carbon atoms. Preferred silsesquioxanes are neutral or anionic silsesquioxanes, prior to addition to the composition. Useful silsesquioxanes can be made by the techniques described in U.S. Pat. No. 3,493,424 (Mohrlok et al.), U.S. Pat. No. 4,351,736 (Steinberger et al.), U.S. Pat. No. 5,073,442 (Knowlton et al.) U.S. Pat. No. 4,781,844 (Kortmann, et al), and U.S. Pat. No. 4,781,844. A coating solution preferably comprises at least 90 wt. %, preferably at least 95 wt. %, and more preferably at least 99.5 wt. % silsesquioxane, relative to total solids (i.e. fluorochemical urethane of Formula I and silsesquioxane).

The silsesquioxanes may be prepared by adding silanes to a mixture of water, a buffer, a surface active agent and optionally an organic solvent, while agitating the mixture under acidic or basic conditions. It is preferable to add the quantity of silane uniformly and slowly in order to achieve a narrow particle size of 200 to 500 Angstroms. The exact amount of silane that can be added depends on the substituent R and whether an anionic or cationic surface-active agent is used. Co-condensates of the silsesquioxanes in which the units can be present in block or random distribution are formed by the simultaneous hydrolysis of the silanes. The amount of tetraorganosilanes, including tetralkoxysilanes and hydrosylates thereof (e.g. of the formula $Si(OH)_4$) present is less than 10 wt. %, preferably less than 5 wt. %, more preferably less than 2 wt. % relative to the weight of the silsesquioxane.

The following silanes are useful in preparing the silsesquioxanes of the present invention: methyltrimethoxysilane, methyltriethoxysilane, methyltriisopropoxyoxysilane, ethyltrimethoxysilane, ethyltriethoxysilane, propyltrimethoxysilane, isobutyltrimethoxysilane, isobutyltriethoxysilane, 2-ethylbutyltriethoxysilane, and 2-ethylbutoxytriethoxysilane.

The composition may be applied to the substrate by conventional techniques such as, for example, spraying, knife coating, notch coating, reverse roll coating, gravure coating, dip coating, bar coating, flood coating, or spin coating. Typically, the polymerizable composition is applied to the substrate as a relatively thin layer resulting in a dried cured layer having a thickness in a range of from about 40 nm to about 60 nm, although thinner and thicker (e.g., having a thickness up to 100 micrometers or more) layers may also be used. Next, any optional solvent is typically at least partially removed (e.g., using a forced air oven), and the composition is then at least partially cured to form a durable coating.

A preferred coating method for application of a fluorinated isocyanate silane of the present invention includes spray application. A substrate to be coated can typically be contacted with the treating composition at room temperature (typically, about 20 to about 25° C.). Alternatively, the mixture can be applied to substrates that are preheated at a temperature of for example between 60 and 150° C. This is of particular interest for industrial production, where e.g. ceramic tiles can be treated immediately after the baking oven at the end of the production line. Following application, the treated substrate can be dried and cured at ambient or elevated temperature, e.g. at 40 to 300° C. and for a time sufficient to dry. The process may also require a polishing step to remove excess material.

The present invention provides a protective coating on substrate that is relatively durable, and more resistant to contamination and easier to clean than the substrate surface itself. The present invention provides in one embodiment a method and composition for use in preparing a coated article comprising a substrate, preferably a hard substrate, and an antisoiling coating of greater than a monolayer (which is typically greater than about 15 Angstroms thick deposited thereon. Preferably an antisoiling coating of the present invention is at least about 20 Angstroms thick, and more preferably, at least about 30 Angstroms thick. Generally, the thickness of the coating is less than 10 micrometers, preferably less than 5 micrometers. The coating material is typically present in an amount that does not substantially change the appearance and optical characteristics of the article.

EXAMPLES

Objects and advantages of this invention are further illustrated by the following examples, but the particular materials and amounts thereof recited in these examples, as well as other conditions and details, should not be construed to unduly limit this invention. These examples are merely for illustrative purposes only and are not meant to be limiting on the scope of the appended claims.

All parts, percentages, ratios, etc. in the examples and the rest of the specification are by weight, unless noted otherwise. Solvents and other reagents used were obtained from Aldrich Chemical Company, Milwaukee, Wis. unless otherwise noted.

Test Methods
Nuclear Magnetic Resonance (NMR)
$^1$H and $^{19}$F NMR spectra were run on a Varian UNITYplus 400 Fourier transform NMR spectrometer (available from Varian NMR Instruments, Palo Alto, Calif.).

IR Spectroscopy (IR)
IR spectra were run on a Thermo-Nicolet, Avatar 370 FTIR, obtainable from Thermo Electron Corporation, Waltham, Mass.

Method for Forming Coatings on Polycarbonate Plaques

Polycarbonate plaques (10 cm by 10 cm) were coated with coating compositions comprising fluorochemical urethane compositions according to this invention using the dip coating process. To form the coatings, each polycarbonate plaque was first immersed into a SHP 401 primer at a rate of 90 cm per minute rate. Once the entire plaque was immersed in the primer, the plaque was removed from the primer a rate of 90 cm per minute rate and was allowed to air dry at room temperature for 10 minutes. The dried plaque was then immersed into a solution of SHC-1200 or a solution of SHC-1200 containing 0.3 weight percent of a fluorochemical urethane silane prepared according to this invention. The plaque was immersed in to the coating solution at a rate of 90 cm per minute and withdrawn out at 19 cm per minute, air dried at room temperature for 20 minutes and finally heated in an oven for 30 minutes at 130° C.

Ink Repellency Test

This test was used to measure the ink repellency of the coatings on polycarbonate plaques. Coated polycarbonate plaques were prepared as described above. A line was drawn across the surface of a coated polycarbonate plaque a Sharpie™ Fine Point, Series 30000 permanent marker (available from Sanford, a division of Newell Rubbermaid) The samples were rated for appearance and for the ability to repel a black Sharpie marker.

| Ink Repellency Test Ratings | |
|---|---|
| Ranking | Description |
| 1 | Ink beaded well |
| 2 | Some beading |
| 3 | Little beading |
| 4 | No beading |

Ink Repellency Durability Test

To measure the durability of ink repellency of coated polycarbonate plaques a modified Oscillating Sand Method (ASTM F 735-94) was used. A coated polycarbonate plaque (i.e., test sample prepared as described above) was secured using vinyl tape and rubber bands onto a jar, with an 87 mm inner diameter (VWR 36318-860, commercially available from VWR Bristol, Conn.), containing 50 grams of unused 20-30 mesh Ottawa sand (obtained from VWR, Bristol, Conn.). The jar was placed in a shaker (VWR DS-500E, obtained from VWR Bristol, Conn.) with the side containing the test sample at the bottom and the shaker was operated oscillating at a rate of 225 rpm for 10 minutes. At the end of ten minutes, the polycarbonate plaque was removed and a Sharpie permanent marker was used to draw a line across its surface that was in contact with the sand. The normalized (%) length of the 87 mm ink line that did not bead up was measured and reported as percent ink repellency loss. The data reported is the average of three independent tests.

Taber Haze Test

This test was run on polycarbonate plaques coated as described above. The test procedure was that of Procedure No CET-APRS-STP-0316, Revision 1.1, dated 24 Oct. 2005 by National Institute of Occupational Safety and Health. A number less than 4 is desired.

Steel Wool Durability Test

The abrasion resistance of the coated and cured polycarbonate plaques (prepared as described above) were tested cross-web to the coating direction by use of a mechanical device capable of oscillating a steel wool sheet adhered to a stylus across the film's surface. The stylus oscillated over a 90 mm wide sweep width at a rate of 315 mm/sec (3.5 wipes/sec) wherein a "wipe" is defined as a single travel of 90 mm. The stylus had a flat, cylindrical base geometry with a diameter of 3.2 cm. The stylus was designed to enable attachment of additional weights to increase the force exerted by the steel wool normal to the film's surface. The samples were tested at a 500 g load for 25 wipes. The #0000 steel wool sheets were "Magic Sand-Sanding Sheets" available from Hut Products, Fulton, Mo. The #0000 has a specified grit equivalency of 600-1200 grit sandpaper. The 3.2 cm steel wool discs were die cut from the sanding sheets and adhered to the 3.2 cm stylus base with 3M Brand Scotch Permanent Adhesive Transfer tape. The contact angles were measured on the wear track after the steel wool abrasion, and on an area of the plaque adjacent to the wear track that was not effected by the steel wool track (i.e., before steel wool testing). The contact angle measurements were made using the "method for Measuring Contact Angles" as described below. The reported data represents the average of measurements done on three plaques. Three drops were placed on each plaque, with contact angle measured on the right and the left sides of each of the drops.

Method for Measuring Contact Angles

The coated polycarbonate plaques (prepared as described above) were rinsed for 1 minute by hand agitation in IPA before being subjected to measurement of water contact angles. Measurements were made using as-received reagent-grade hexadecane and de-ionized water filtered through a filtration system (obtained from Millipore Corporation Billerica, Mass.), on a video contact angle analyzer (available as product number VCA-2500XE from AST Products Billerica, Mass.). Reported values are the averages of measurements on at least three drops measured on the right and the left sides of the drops. Drop volumes were 5 µL for static measurements.

Solvent Resistance Test

Four chambers were filled with a different solvent: ethanol, isopropanol, toluene and MEK. Each plaque prepared as described above was placed in all four chambers for 60 seconds. Observations such as de-lamination, cracks, discoloration, and any other changes in the coating were recorded. Each plaque was then placed in the solvent chambers for an additional 300 seconds. All observations were again recorded.

Materials

Hexamethylene diisocyanate (Desmodur™ N100) was obtained from Bayer Polymers LLC of Pittsburgh, Pa.

Hexamethylene diisocyanate (Desmodur™ N3300A) was obtained from Bayer Polymers LLC of Pittsburgh, Pa.

Methylisobutylketone (MIBK) was obtained from Burdick & Jackson Solvents, a unit of Honeywell International, Inc. Morris Township, N.J.

1,4-diazabicyclo[2.2.2]octane, DABCO™33LV, available from Air Product and Chemicals, Inc., Allentown, Pa.

2,2'-azobis(2-methylbutyronitrile)(Vazo™ 67) was obtained from EI DuPont de Nemours & Co., Wilmington, Del.

MeFBSE ($C_4F_9SO_2N(CH_3)CH_2CH_2OH$) was prepared by essentially following the procedure described in U.S. Pat. No. 6,664,354 (Savu et al.), Example 2, Part A.

HFPO—$C(O)N(H)CH_2CH_2OH$ (HFPOAmidol) was prepared by a procedure similar to that described in U.S. Pat. No. 7,094,829 (Audenaert et al.), entitled "Fluorochemical Composition Comprising a Fluorinated Polymer and Treatment of a Fibrous Substrate Therewith".

Pentaerythritol Triacrylate ($PET_3A$) was obtained from Sartomer Company of Warrington, Pa.

Poly(methyl methacrylate) Primer (SHP™ 401) was obtained from GE Silicones of Waterford, N.Y.

Methylsilsesquioxane solution (SHC™ 1200) was obtained from GE Silicones of Waterford, N.Y.

N-methyl Aminopropyltrimethoxy silane (MAPTMS) was obtained from Union Carbide Chemicals and Plastics Co. of Danbury, Conn.

Bis(propyl-3-trimethoxysilane) amine was obtained from Gelest, Morrisville, Pa.

Aminopropyltrimethoxy silane, (APTMS) was obtained from Sigma-Aldrich, Milwaukee, Wis.

Mercaptopropyltrimethoxysilane was obtained from Sigma-Aldrich, Milwaukee, Wis.

Pentaerythritol triallyl ether was obtained from Sigma-Aldrich, Milwaukee, Wis. as a 70% technical grade solution.

Hydroxyethyl acrylate (HEA) was obtained from Sigma-Aldrich, Milwaukee, Wis.

Dibutyltin dilaurate (DBTDL) was obtained from Sigma-Aldrich, Milwaukee, Wis.

Polycarbonate Plaques were molded by Minnesota Mold & Engineering, Vadnais Heights, Minn. (from GE Lexan™ 101, Mount Vernon, Ind.).

Example 1

30 g, 0.15 eq isocyanate DESMODUR N3300A, 40.3 g, 0.05 mol HFPO amidol, 43.8 g solution (containing 31 g, 0.12 mol) of pentaerythritol allyl ether, and 445 g MIBK were charged into 1 L flask. The mixture was heated to 80° C. while stirring and a solution was formed. The solution was purged with $N_2$ for 1 minute and three drops each of DBTDL and DABCO 33LV were added to it. The resulting solution was then heated to 110° C. for 15 hours. At the end if the 15 hours, the IR spectrum of a sample had no peaks corresponding to a NCO group. The solution was then allowed to cool to 70° C. and 70.7 g, 0.36 mol mercaptopropyltrimethoxysilane was added to it. After the solution was purged with $N_2$ for 3 minutes and 0.7 g Vazo 67 was added to it, the solution was heated for 16 hours at 70° C. Following this period, there were no allylic groups remaining as determined from IR spectrum of a sample. The product fluorochemical urethane silane was a golden solution with 28% solids content.

Example 2

30 g, 0.15 eq isocyanate DESMODUR N3300A, 40.3 g, 0.05 mol HFPO amidol, 10.7 g, 0.03 mol MeFBSE, 33 g solution (containing 23 g, 0.09 mol) of pentaerythritol allyl ether, and 445 g MIBK were charged into a 1 L flask. The mixture was heated to 80° C. while stirring and a solution was formed. The solution was purged with $N_2$ for 1 minute and three drops each of DBTDL and DABCO 33LV were added to it. The resulting solution was heated to 110° C. for 15 hours. At the end of the 15 hours, the IR spectrum of a sample had no peaks corresponding to a NCO group. The solution was then allowed to cool to 70° C. and the 53 g, 0.26 mol mercaptopropyltrimethoxysilane was added to it. After the resulting solution was purged with $N_2$ for 3 minutes and 0.7 g Vazo 67 was added to it, the solution was heated at 70° C. for 16 hours. Following this period, there were no allylic groups remaining as determined from IR spectrum of a sample. The product fluorochemical urethane silane was a golden solution with 25% solids content.

Example 3

30 g, 0.15 eq isocyanate DESMODUR N100, 28.6 g, 0.05 mol HFPO amidol, 43.8 g solution (containing 31 g, 0.12 mol) of pentaerythritol allyl ether, and 445 g MIBK were charged into a 1 L flask. The mixture was heated to 80° C. while stirring and a solution was formed. The solution was purged with $N_2$ for 1 minute and three drops each of DBTDL and DABCO 33LV were added it. The resulting solution was heated to 110° C. for 15 hours. At the end of the 15 hours, the IR spectrum of a sample had no peaks corresponding to a NCO group. The solution was then allowed to cool to 70° C. and 70.7 g, 0.36 mol of mercaptopropyltrimethoxysilane was added to it. After the resulting solution was purged with $N_2$ for 3 minutes and 0.7 g Vazo 67 was added to it, the solution was heated at 70° C. for 16 hours. Following this period, there were no allylic groups remaining as determined from IR spectrum of a sample. The product fluorochemical urethane silane was a golden solution with 27.2% solids content.

Example 4

28.6 g, 0.15 eq isocyanate DESMODUR N100, 40.3 g, 0.05 mol HFPO amidol, 10.7 g, 0.03 mol MeFBSE, 33 g solution (containing 23 g, 0.09 mol) of pentaerythritol allyl ether, and 445 g MIBK were added into a 1 L flask. The mixture heated to 80° C. while stirring and a solution was formed. The solution was purged with $N_2$ for 1 minute and three drops each of DBTDL and DABCO 33LV were added to it. The resulting solution was heated to 110° C. for 15 hours. At the end of the 15 hours, the IR spectrum of a sample had no peaks corresponding to a NCO group. The solution was then allowed to cool to 70° C. and 53 g, 0.26 mol mercaptopropyltrimethoxysilane was added to it. After the resulting solution was purged with $N_2$ for 3 minutes and 0.7 g Vazo 67 was added to it, the solution was heated at 70° C. for 16 hours. Following this period, there were no allylic groups remaining as determined from IR spectrum of a sample. The product fluorochemical urethane silane was a golden solution with 25.6% solids content.

Example 1-4 materials were used to prepare coatings on polycarbonate plaques according to the "Method for Forming Coatings on Polycarbonate Plaques" described above. The performances of the resulting coatings were then evaluated using Taber Haze Change, Ink Repellency Test, Ink Repellency Durability Test, Steel Wool Test and Solvent Test as described above.

Table 1 below summarizes the results of Taber Haze Test, Ink Repellency Test and Ink Repellency Durability Test for coatings made using SHC-1200 with no added fluorochemical urethane silane and Example 1-4 materials.

TABLE 1

| Example | Taber Haze Test | Ink Repellency Test | Ink Repellency Durability Test, % |
|---|---|---|---|
| SHC-1200 control | 3.57 | 4 | 100 |
| 1 | 3.59 | 2.5 | 100 |
| 2 | 3.88 | 1 | 57 |
| 3 | 3.24 | 1 | 72 |
| 4 | 3.50 | 1 | 87 |

Table 2 below summarizes the results of Steel Wool Test for coatings made using SHC-1200 with no added fluorochemical urethane silane and Example 1-4 materials.

TABLE 2

| | Before Steel Wool Test | | After Steel Wool Test | |
|---|---|---|---|---|
| Example | Contact Angle | Standard Deviation | Contact Angle | Standard Deviation |
| SHC-1200 control | 94.1 | 1.3 | 87.6 | 1.9 |
| 1 | 99.5 | 0.5 | 97 | 1.3 |
| 2 | 106.5 | 0.6 | 104.4 | 1.5 |
| 3 | 101.1 | 1.2 | 99.5 | 1.0 |
| 4 | 102.5 | 0.8 | 100.9 | 1.1 |

Table 3 below summarizes the results of Solvent Test for coatings made using SHC-1200 with no added fluorochemical urethane silane and Example 2-4 materials.

TABLE 3

| Example | Solvent | After 60 seconds | After 300 seconds |
|---|---|---|---|
| SHC-1200 control | Ethanol | No effect | No effect |
| SHC-1200 control | Isopropanol | No effect | No effect |
| SHC-1200 control | Toluene | No effect | No effect |
| SHC-1200 control | MEK | No effect | Few tiny cracks by edges |
| 2 | Ethanol | No effect | No effect |
| 2 | Isopropanol | No effect | No effect |
| 2 | Toluene | Few tiny cracks | Larger cracks in coating |
| 2 | MEK | Tiny cracks and white spots | Larger cracks and white spots all over coating |
| 3 | Ethanol | No effect | No effect |
| 3 | Isopropanol | No effect | No effect |
| 3 | Toluene | No effect | Few small white spots but no cracks |
| 3 | MEK | Some white spots | White spots and cracks all over coating, de-lamination |
| 4 | Ethanol | No effect | No effect |
| 4 | Isopropanol | No effect | No effect |
| 4 | Toluene | No effect | Cracks and some de-lamination by edges |
| 4 | MEK | Few tiny cracks | White spots and cracks all over coating, de-lamination |

The invention claimed is:
1. A compound of the formula

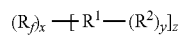

wherein $R_f$ is

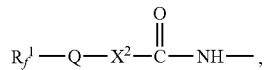

where
$R_f^1$ is a monovalent perfluoroalkyl or a perfluorooxyalkyl group where z is 1, or a divalent perfluoroalkylene or a perfluorooxyalkylene group where z is 2, Q is a covalent bond, or a polyvalent alkylene group of valency z, said alkylene optionally containing one or more catenary (in-chain) nitrogen or oxygen atoms, and optionally containing one or more sulfonamide, carboxamido, or carboxy functional groups;

$X^2$ is —O—, —$NR^4$— or —S—, where $R^4$ is H or $C_1$-$C_4$ alkyl, $R^1$ is the residue of a polyisocyanate selected from multivalent aliphatic, alicyclic, or aromatic moiety, $R^2$ is of the formula:

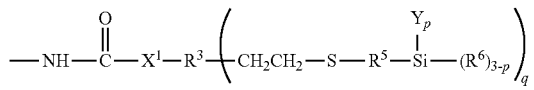

wherein $X^1$ is —O— or —$NR^4$—, where $R^4$ is H or $C_1$-$C_4$ alkyl, $R^3$ is a polyvalent alkylene or arylene groups, or combinations thereof, said alkylene groups optionally containing one or more catenary oxygen atoms;

$R^5$ is a divalent alkylene group, said alkylene groups optionally containing one or more catenary oxygen atoms;

Y is a hydrolysable group selected from a halogen, a $C_1$-$C_4$ alkoxy group, or a $C_1$-$C_4$ acyloxy group, $R^6$ is a monovalent alkyl or aryl group, p is 1, 2 or 3, and q is 1 to 5, x and y are each independently at least 1, and z is 1 or 2.

2. The compound of claim 1 wherein $R_f^1$ is a perfluorooxyalkylene group comprising perfluorinated repeating units selected from the group consisting —$(C_nF_{2n}O)$—, —(CF(Z)O)—, —$(CF(Z)C_nF_{2n}O)$—, —$(C_nF_{2n}CF(Z)O)$—, —$(CF_2CF(Z)O)$—, and combinations thereof, wherein n is 1 to 4 and Z is a perfluoroalkyl group, or a perfluoroalkoxy group.

3. The compound of claim 1 wherein z is 1 and $R_f^1$ is a monovalent group of the formula F—$R_f^3$—O—$R_f^4$—$(R_f^5)_q$— or wherein z is 2 and $R_f^1$ is a divalent group of the formula:

—$R_f^3$—O—$R_f^4$—$(R_f^5)_q$—, wherein $R_f^3$ represents a perfluoroalkylene group, $R_f^4$ represents a perfluoroalkyleneoxy group having 1, 2, 3 or 4 carbon atoms or a mixture of such perfluoroalkyleneoxy groups, $R_f^5$ represents a perfluoroalkylene group, and q is 0 or 1.

4. The compound of claim 1 wherein said perfluorooxyalkylene group is selected from one or more of —[$CF_2$—$CF_2$—O]$_r$—; —[$CF(CF_3)$—$CF_2$—O]$_s$—; —[$CF_2CF_2$—O]$_r$—[$CF_2O$]$_t$—; —[$CF_2CF_2CF_2CF_2$—O]$_u$— and —[$CF_2$—$CF_2$—O]$_r$—[$CF(CF_3)$—$CF_2$—O]$_s$—; wherein each of r, s, t and u each are integers of 1 to 50.

5. The compound of claim 1 wherein $R_f$ is a monovalent perfluorooxyalkylene group and z is 1.

6. The compound of claim 1 wherein the molar ratio of silane groups to —NH—C(O)—$X^1$— groups is greater than 1:1.

7. The compound of claim 1 wherein $R_f$ is derived from a fluorinated polyol.

8. The compound of claim 1, derived from the free-radical addition of a thiosilane to an ethylenically unsaturated group.

9. A coating composition comprising at least one compound of claim 1 and a solvent.

10. The composition of claim 9 further comprising a silsesquioxane.

11. A composition comprising an aqueous dispersion or suspension of the compounds of claim 1.

12. A compound of claim 1 comprising the free radical reaction product of a thiosilane with a fluorochemical urethane compound having pendent ethylenically unsaturated groups, said fluorochemical urethane compound comprising the reaction product of a polyisocyanate, a nucleophilic fluorinated compound, and a nucleophilic ethylenically unsaturated compound.

13. A method of preparing the compound of claim 1 comprising the step of free radical addition of a thiosilane to a urethane compound of the formula:

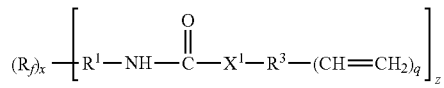

wherein $R_f$ is

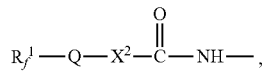

where $R_f^1$ is a monovalent perfluoroalkyl or a perfluorooxyalkyl group where z is 1, or a divalent perfluoroalkylene or a perfluorooxyalkylene group where z is 2, $R^1$ is the residue of a polyisocyanate selected from multivalent aliphatic, alicyclic, or aromatic moiety, $X^1$ is —O— or —$NR^4$—, where $R^4$ is H or $C_1$-$C_4$ alkyl, $R^3$ is a polyvalent alkylene or arylene groups, or combinations thereof, said alkylene groups optionally containing one or more catenary oxygen atoms;

z is 1 or 2, and q is 1 to 5.

14. The method of claim 13 wherein the thiosilane is of the formula

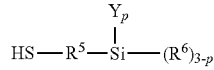

wherein $R^5$ is a divalent alkylene group, said alkylene group optionally containing one or more catenary oxygen atoms;

Y is a hydrolysable group selected from a halogen, a $C_1$-$C_4$ alkoxy group, or a $C_1$-$C_4$ acyloxy group, $R^6$ is a monovalent alkyl or aryl group, and p is 1, 2 or 3.

* * * * *

UNITED STATES PATENT AND TRADEMARK OFFICE
CERTIFICATE OF CORRECTION

PATENT NO. : 8,002,886 B2
APPLICATION NO. : 12/444863
DATED : August 23, 2011
INVENTOR(S) : Gregory D Clark Page 1 of 1

It is certified that error appears in the above-identified patent and that said Letters Patent is hereby corrected as shown below:

Column 11,
Line 10, delete "$(Y)_p(R^6)_{3-p}]_{q(IX)}$" and insert -- $(Y)_p(R^6)_{3-p}]_q(IX)$ --.

Column 21,
Line 40, delete "$R_f^l$" and insert -- $R_f^1$ --.

Signed and Sealed this
First Day of November, 2011

David J. Kappos
*Director of the United States Patent and Trademark Office*